United States Patent [19]
Limacher et al.

[11] Patent Number: 5,702,476
[45] Date of Patent: Dec. 30, 1997

[54] ARTIFICIAL JOINT SHELL

[75] Inventors: Urs Limacher, Hünenberg; Stefan Lamprecht, Birchwil, both of Switzerland

[73] Assignees: Sulzer Medizinaltechnik AG, Winterthur; Allo Pro AG, Baar, both of Switzerland

[21] Appl. No.: 632,978

[22] Filed: Apr. 16, 1996

[30] Foreign Application Priority Data

May 18, 1995 [EP] European Pat. Off. .............. 95810329

[51] Int. Cl.$^6$ ................................. A61F 2/34; A61F 2/30
[52] U.S. Cl. ..................................... 623/22; 623/18
[58] Field of Search ........................ 623/16, 17, 18, 623/19, 22, 23

[56] References Cited

U.S. PATENT DOCUMENTS

| Re. 28,895 | 7/1976 | Noiles ........................... 623/22 |
| 4,695,282 | 9/1987 | Forte et al. ...................... 623/22 |
| 4,961,748 | 10/1990 | Frey et al. ....................... 623/22 |
| 5,049,158 | 9/1991 | Engelhardt et al. ............... 623/22 |
| 5,282,864 | 2/1994 | Noiles ........................... 623/22 |
| 5,480,448 | 1/1996 | Mikhail .......................... 623/22 |

FOREIGN PATENT DOCUMENTS

| 0549483 | 6/1993 | European Pat. Off. ............. 623/22 |
| 0 649 641 | 4/1995 | European Pat. Off. . |
| 4429026 | 2/1995 | Germany . |

*Primary Examiner*—Debra S. Brittingham
*Attorney, Agent, or Firm*—Townsend, and Townsend and Crew LLP

[57] ABSTRACT

The invention relates to an artificial joint shell having an outer shell (2) which is implantable in a bone base and a retro-fittable inner shell (3), the inner and outer shells being fixable to one another via a friction-locked clamping force (5), preferably via a self-locking, conical connection. A tunnel (6) is formed in the partition surface (4) between the two shells (2, 3) and connects two points at the shell edge in an arc (37) that extends towards the shell base (7). A wire (8) is threaded through the tunnel (6), and by applying an extraction force to the wire the inner shell (3) is extracted. The extraction force is uniformly applied to the inner insert along the arc (37) prescribed by the tunnel and does not damage the inner shell.

18 Claims, 4 Drawing Sheets

ARTIFICIAL JOINT SHELL

BACKGROUND OF THE INVENTION

The invention relates to an artificial joint shell having an outer shell and an inner shell, the inner shell having a partition surface common to the outer shell and being anchorable in the outer shell with a clamped connection.

Paired artificial joint shells with a snap connection between the outer and inner joint shells have been in use for many years. Especially for inner shells made of plastic, use is made of the low stiffness of the plastic in order to achieve a form lock in the snap connection. For example, patent document EP 0 245 527 discloses a plastic journalling shell in a metallic outer shell secured to each other by a snap connection formed with friction and form-locking. As a result of the low stiffness of the plastic, deviations in the dimensions on manufacture only slightly affect the retension forces between the two shells when they are paired together. In many shell connection systems, the removal of the plastic inner shell inevitably leads to its destruction or the destruction of an intermediate member. This becomes more of a problem when the inner and outer shells are made of metal, since the manufacturing tolerances for their pairing in the clamped connection have to be substantially more stringent. Furthermore, the extraction forces for removing an inner shell out of an implanted outer shell cannot be allowed to be so large that the seating in the bone of the implanted outer shell becomes endangered. Screw drives for extracting or pressing out the inner shell can only be used when the material of the inner shell and the thickness of the inner shell allow threaded bores for the extraction to be fitted therein, or when the inner shell is provided with a flange having threaded bores. These conditions are, however, difficult to achieve when wear-resistant mounting materials, such as for example ceramics or hard metal alloys, are used.

SUMMARY OF THE INVENTION

It is therefore an object of the invention to provide a system which allows the connection between the outer shell and the inner shell to be established and released in a simple manner for various material combinations for the outer and inner shells. This object is satisfied in that the clamped connection is formed by a friction lock between the inner shell and the outer shell; and in that a tunnel is formed in the partition surface or interface between the inner and outer shells and connects two points at the shell edge in an arc towards the shell base, in order to pull the inner shell out of the outer shell against the retension forces of the friction locking by means of a wire that can be passed through the tunnel.

An arrangement of this kind has the advantage that the connection from the inner shell to the outer shell can be established with a light knock after the shells have been brought together and that, even when large retension forces exist between the shells, the tunnel provides a sufficiently large surface to ensure that, on extraction, a uniform loading of the inner shell along the arc is achieved. It is thus possible with a single conical angle for the self-locking connection to use inner shells made of different materials and inner shells having different extraction forces in a given outer shell.

When the inner shell has thin walls or is difficult to work, the channel or flute forming the tunnel can be set into the outer shell. For inner shells with thick walls, the channel can be provided on the inner shell.

Since the pressing forces arising on the inner shell on extraction are uniformly distributed, it is possible to use brittle materials for the inner shell. Furthermore, it is possible to use flangeless inner shells and inner shells having a rotationally symmetric form on the outer side. This brings production advantages for materials which are difficult to work. Pliers supported on the outer shell for pulling the wire to reduce the length of the wire arc lying in the tunnel are suitable for use as the extraction tool. The extraction force and the supporting force thus act directly adjacent to one another via the inner shell and the extraction apparatus. When a non-compensated, residual individual force acting on the extraction apparatus is necessary for performing a reduction in length of the wire arc, this force, which at the end acts on the implanted outer shell, can be kept small insofar as the movement associated with the force is kinematically reduced; i.e. geared down.

Moreover, the conical, self-locking connection has the advantage that inner shells can be employed which have a one-sided raised edge. Other kinds of asymmetry can be fitted at any rotational angle in an implanted outer shell. Their rotational position can then be corrected by the relatively simple extraction.

DESCRIPTION OF THE PREFERRED EMBODIMENTS

The Figures show an artificial joint socket having an outer shell which can be implanted in a bone base and an inner shell which can be retro-fitted thereinto. The inner and outer shells are held together by a friction-locked clamping force, and preferably via a self-locking conical connection. A tunnel is formed in the partition surface between the two shells. The tunnel connects two points at the shell edge with an arc oriented towards the shell base. A wire can be threaded through the tunnel in order to allow the inner shell to be extracted with an extraction force that is uniformly distributed over the arc to avoid damaging the shell.

Figure 1:
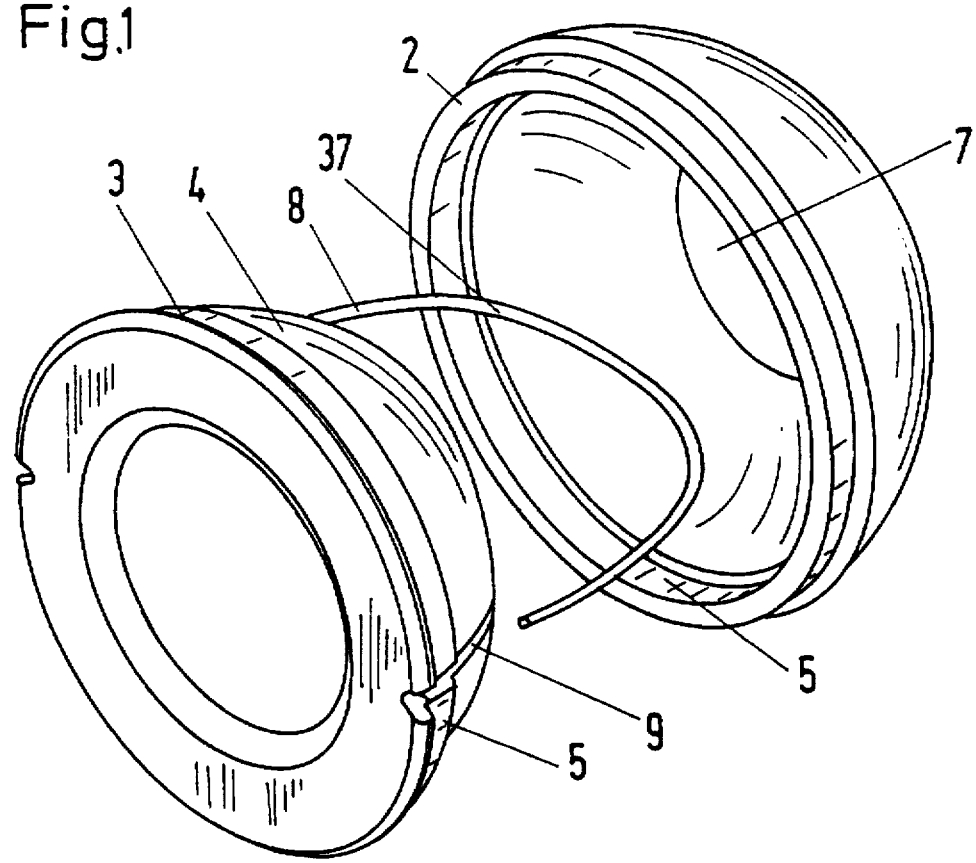
FIG. 1 is a schematic exploded view of an inner shell having a channel, an extraction wire threaded in an arc in this channel; and a corresponding outer shell.
Figure 2:
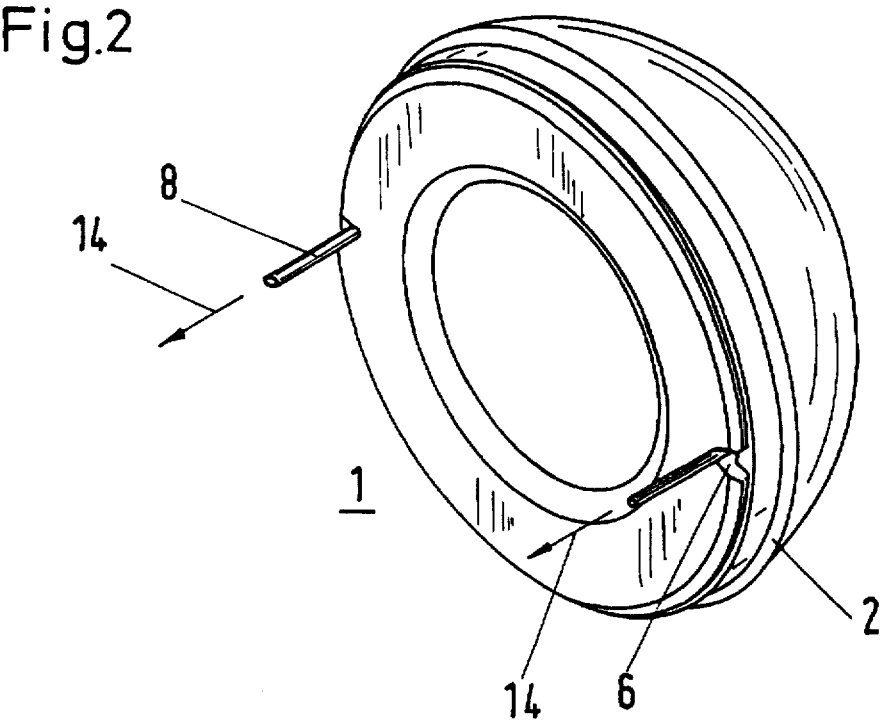
FIG. 2 is a schematic illustration of the elements of FIG. 1 in the assembled state.
Figure 3:
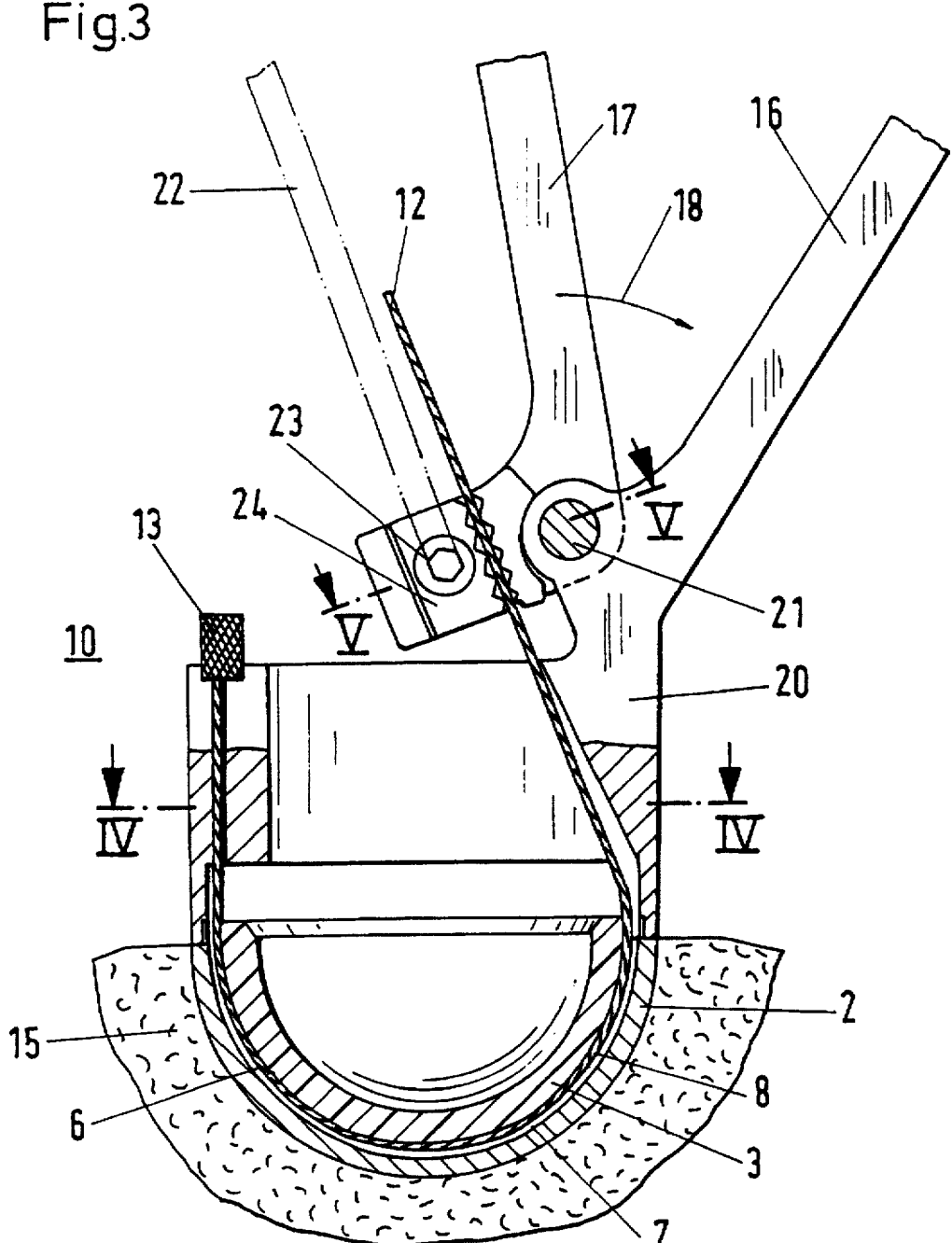
FIG. 3 is a schematic illustration of an example for an extraction apparatus located on an implanted outer shell for extracting a fitted inner shell.
Figure 4:
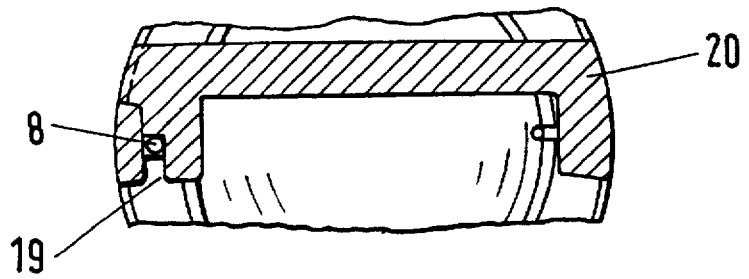
FIG. 4 is a schematic illustration taken along line IV—IV in FIG. 3.
Figure 5:
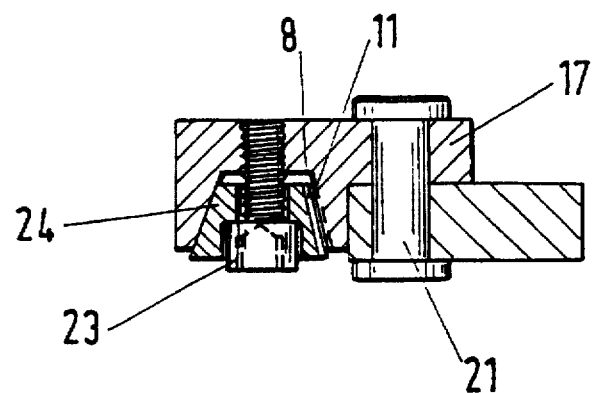
FIG. 5 is a schematic illustration taken along line V—V in FIG. 3.

In FIGS. 1 and 2, an inner shell 3 is connectable to an outer shell 2 via a self-locking conical connection 5. A tunnel 6 is produced in the assembled state in the partition surface 4 between the shells 2, 3. This tunnel connects two points at the shell edge along an arc 37 that extends towards the shell base 7. In this case, the tunnel 6 is formed by a channel 9 in the outer surface of the inner shell 3 and by the partition surface 4. The tunnel could just as well be formed by a channel in the inner surface of the outer shell 2 and the partition surface 4 on the inner shell 3. The wire 8 is elastic and flexible in the manner of a piano wire or a multi-wire cable in a Bowden cable. When tension on the wire 8 is produced relative to the outer shell 2 in the extraction direction 14, the extraction force distributes itself on the inner shell along arc 37. Tension can be produced with solid extraction apparatuses supported on the outer shell or alternatively with a flexible Bowden cable, the guide sleeve of which is supported on the outer shell.

In FIGS. 3 to 7, the principle of a solid extraction apparatus 10 is shown. The extraction apparatus 10 comprises a placement body 20 which sits at both ends of the tunnel on the outer shell 2 with a foot 25. At one end, the wire 8 is anchored in the placement body 20 with a head 13. The wire is guided through the tunnel 6 of the joint shell and held at its other end in a clamping lever 17 which is pivotable about a journalling spigot 21.

Figure 6:
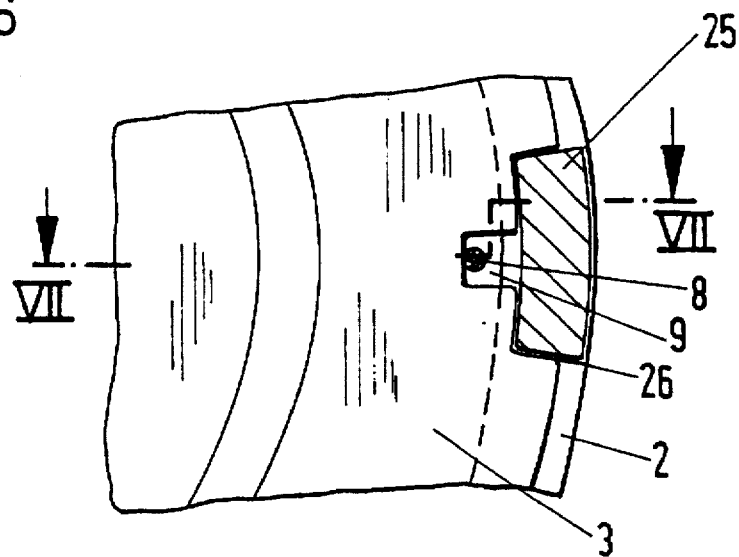
FIG. 6 is a schematic illustration of an enlarged portion of FIG. 4.
Figure 7:
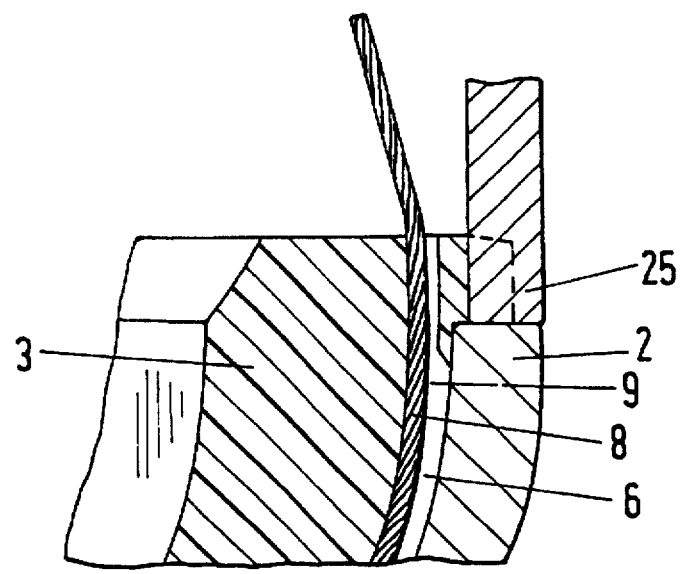
FIG. 7 is a schematic illustration of an enlarged section of FIG. 6.

The clamping point 11 is serrated. The clamping point is made by firmly pulling a conical clamping piece 24 by means of a clamping screw 23 using an Allen key 22 shown in phantom lines. Due to the fact that the clamping point 11 has a shorter distance to the journalling spigot 21 than the point of action of the force on the substantially longer levers 16, 17, the pivotal movement in a pivot direction 18 is reduced so that a smaller force is required. On the simultaneous manual application of a force on the lever 16, 17, the forces compensate each other out for the most part and hardly any additional forces arise between the outer shell 2 and a bone base surrounding it. In order to simplify the handling for the guiding in of the wire 8, the wire is provided with a tip 12 which allows the wire 8 to be threaded into the tunnel 6, initially without the placement body 20. The placement body 20 comprises lateral grooves 19 or cut-outs and a laterally open clamping point 11, in order to guide the wire 8, which has already been threaded in, laterally into the extraction apparatus. In FIG. 6, the edge of the inner shell 3 is provided with a cut-out 26 in the region of the channel 9 in order to center the foot 25 of the extraction apparatus on the edge of the outer shell 2.

Figure 8:
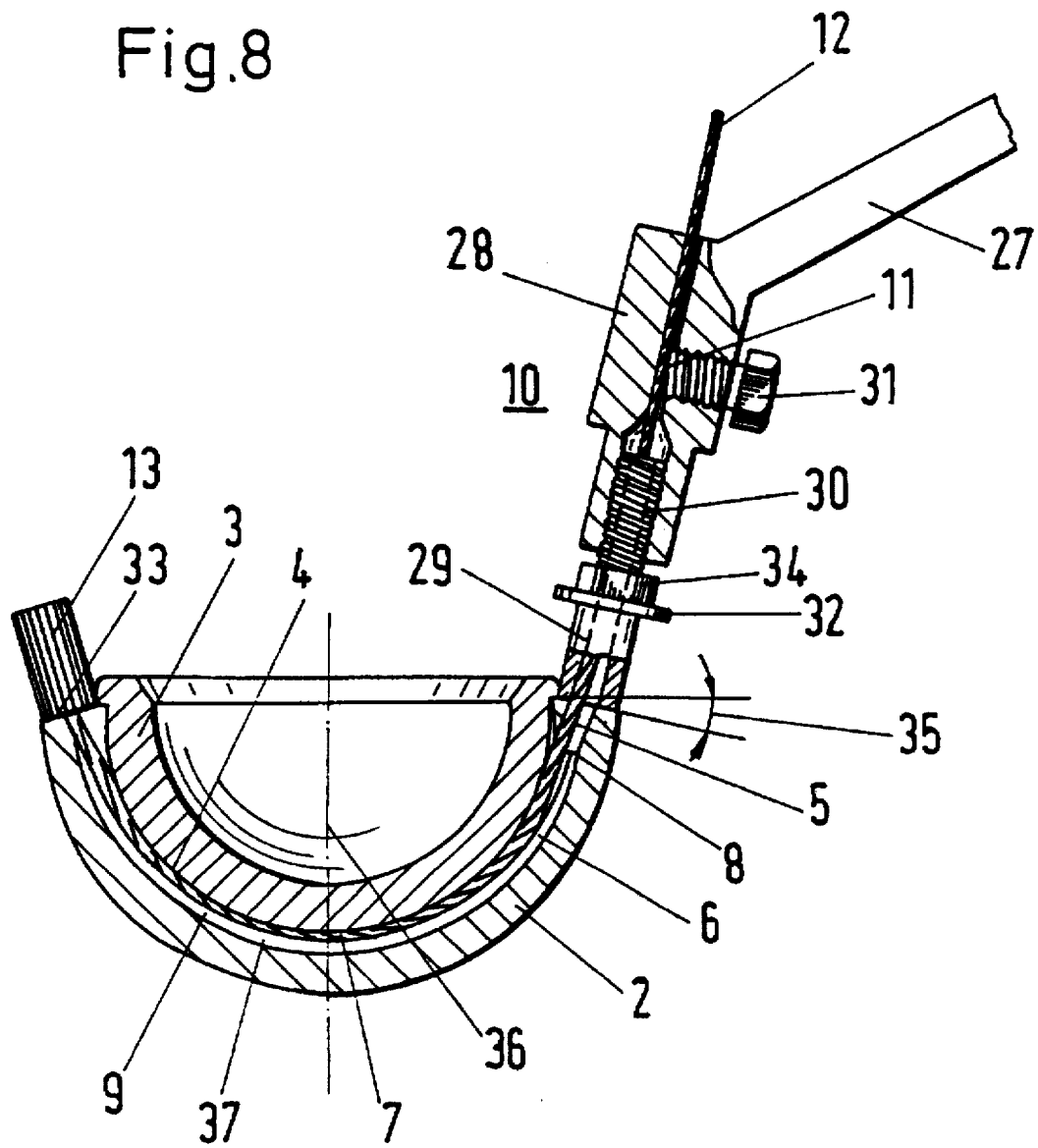
FIG. 8 is a schematic illustration of an extraction apparatus having a screw drive for producing the extraction force.

A further possible design for the extraction apparatus 10 is shown in FIG. 8. A channel 9 is located in the outer shell 2 and forms a tunnel 9 together with the smooth inner shell 3. A wire 8 having a tip 12 and head 13 is directly threaded in. An inclined portion 33 having an angle 35 at the edge of the outer shell 2 forms an abutment surface for the head 13 and for a lower part 29 in the form of a hollow screw. The hollow screw is screwed into an upper part 28 of the extraction apparatus 10 via a thread 30. Upper and lower parts 28, 29 are reversely drawn over the inserted wire 8 and the wire is then clamped to a clamping point 11 with a clamping screw 31. The lower part 29 is now screwed out with an open spanner (not shown) which lies on the shoulder 32 and acts on the surfaces of action 32. Simultaneous with this screwing out, tension is produced on the wire to release the clamped connection 5 between the inner and outer shells. A holding grip 27 on the upper part 28 ensures that a counter-torque is produced for the torque from the open spanner (not shown). Due to the non-straightforward spatial conditions, it is also possible to use a Bowden cable instead of the upper and lower parts 28, 29. The sheath piece of the Bowden cable lies on the outer shell analogous to the lower part 28.

It should be noted quite generally that the arc 37 need not be laid through the pole axes 36 of the inner shell 3 in order to effect a release of the clamped connection 5.

What is claimed is:

1. A replaceable acetabular joint implant comprising an outer shell having a cavity and an inner shell disposed in the cavity, the shells defining an interface between them and a releasable lock which releasably retains the inner shell in the cavity of the outer shell, the outer shell and the inner shell terminating in generally concentric end faces, and a tunnel formed along the interface extending from a first tunnel opening to a second tunnel opening, the tunnel openings being located at at least one of the end faces so that the tunnel is accessible past one of the openings from an exterior of the shells and a flexible tensioning member disposed in said tunnel such that the lock can be released by applying an inner shell releasing force thereto.

2. An implant according to claim 1 wherein the tunnel is defined by a groove formed in a convex exterior surface of the inner shell.

3. An implant according to claim 1 wherein the groove terminates at least in part at the end face of the inner shell.

4. An implant according to claim 1 wherein the groove is formed in a concave inner surface defining the cavity of the outer shell.

5. An implant according to claim 4 wherein the groove terminates at least in part at the end face of the outer shell.

6. An implant according to claim 1 wherein the cavity in the outer shell has a base, and wherein the tunnel extends from the first and second tunnel openings substantially to the base.

7. An implant according to claim 6 wherein the tunnel openings are located substantially diametrically opposite from each other.

8. An implant according to claim 7 wherein the inner shell comprises a ceramic material.

9. An implant according to claim 7 wherein the lock comprises a conical press fit between the inner and the outer shells.

10. In a system for replacing an inner shell of an acetabular joint implant, the implant including an outer shell adapted to be anchored in body tissue and defining a cavity, the inner shell being disposed in the cavity and a lock releasably securing the inner shell to the outer shell when the inner shell is disposed in the cavity and permitting release of the inner shell from the outer shell when a force is applied to the inner shell in a direction away from the outer shell, the improvement comprising a tunnel formed along an interface between the inner shell and the outer shell when the inner shell is in the cavity, the shells defining generally concentric end faces and the tunnel terminating in spaced-apart tunnel openings accessible past the end faces from an exterior of the shells, a flexible tensioning member disposed in the tunnel, having a portion extending through at least one tunnel opening, and being connected with the inner shell, and an extractor having a gripper for gripping the extending portion of the flexible member, a base supporting the gripper and adapted to be placed into force-transmitting contact with the outer shell, and a movement mechanism adapted to apply a force to and move the flexible member with the gripper in a direction generally away from the outer shell to thereby release the lock for removal of the inner shell from the cavity of the outer shell.

11. A system according to claim 10 wherein the base comprises means for transmitting at least a portion of the forces from the base to the outer shell via the end face of the outer shell.

12. A system according to claim 11 wherein the means for transmitting the forces comprises a portion of the base engaging at least a portion of the end face of the outer shell.

13. A system according to claim 10 including a force-reducing device operatively coupled with the base and the gripper for applying a relatively larger force to the flexible member with the gripper by subjecting the movement mechanism to a relatively lesser force.

14. A system according to claim 13 wherein the force-reducing device comprises first and second, pivotable handles of the extractor operatively coupled with the base and the gripper.

15. A system according to claim 13 wherein the force-reducing device comprises a screw drive operatively connecting the actuating movement mechanism with the gripper.

16. A system according to claim 10 wherein the tunnel is formed in a convex exterior surface of the inner shell.

17. A system according to claim 10 wherein the tunnel is formed in a concave interior surface defining the cavity of the outer shell.

18. A system according to claim 10 wherein the inner shell comprises a ceramic material.

* * * * *